United States Patent [19]

Wilk

[11] Patent Number: 5,074,867
[45] Date of Patent: Dec. 24, 1991

[54] SURGICAL INSTRUMENT ASSEMBLY AND RELATED SURGICAL METHOD

[76] Inventor: Peter J. Wilk, 185 West End Ave., New York, N.Y. 10023

[21] Appl. No.: 525,913

[22] Filed: May 18, 1990

[51] Int. Cl.⁵ .............................................. A61B 10/00
[52] U.S. Cl. ..................................... 606/128; 604/93; 604/264; 606/127
[58] Field of Search ............... 606/127, 114, 200, 108, 606/52, 128; 604/93, 317, 318, 319, 175, 264, 22, 20; 128/749, 769, 751

[56] References Cited

U.S. PATENT DOCUMENTS

| 30,471 | 10/1860 | Dudley | 606/127 |
|---|---|---|---|
| 3,834,392 | 9/1974 | Lampman et al. | 606/52 |
| 4,112,932 | 9/1978 | Chiulli | 604/264 |
| 4,223,676 | 9/1980 | Wuchinich et al. | 604/22 |
| 4,525,842 | 6/1985 | Myers | 604/20 |
| 4,880,015 | 11/1989 | Nierman | 128/751 |
| 4,997,435 | 3/1991 | Demeter | 606/127 |

OTHER PUBLICATIONS

Article entitled Management of Indirect Inguinal Hernias by Laparoscopic Closure of the Neck of the Sac by Ralph Ger, Keith Monroe, Roger Duvivier & Abdallah Mishrick from The American Journal of Surgery, vol. 159, Apr. 1990, pp. 370-373.

Primary Examiner—Stephen C. Pellegrino
Assistant Examiner—Glenn K. Dawson
Attorney, Agent, or Firm—R. Neil Sudol; Henry D. Coleman

[57] ABSTRACT

A surgical method comprises the steps of (a) piercing an abdominal wall of a patient to form an opening in the wall, (b) inserting a tubular member through the opening, (c) pushing a inert flexible membrane through the tubular member and into a body cavity of the patient, (d) opening the injected membrane from a collapsed configuration into an at least partially opened configuration, (e) juxtaposing the membrane and an internal organ part of the patient, (f) closing the membrane about the body organ part upon juxtaposition of the membrane and the organ part, and (g) drawing the membrane, together with the enclosed organ part, from the patient's body cavity through the tubular member. An associated surgical kit comprises a tubular member insertable through an opening in an abdominal wall of a patient and a flexible membrane disposed in a collapsed configuration at least partially inside the tubular member. An ejection member is provide for pushing the membrane out of the tubular member into an internal body cavity of the patient. Elongate filaments are connected to the membrane through the tubular member for closing the membrane about a body organ part upon a juxtaposition of the organ part and the membrane and for pulling the membrane from the patient's body cavity through the tubular member.

28 Claims, 5 Drawing Sheets

SURGICAL INSTRUMENT ASSEMBLY AND RELATED SURGICAL METHOD

BACKGROUND OF THE INVENTION

This invention relates to a surgical instrument assembly. This invention further relates to a surgical method. More particularly, this invention relates to a laproscopic method and a surgical instrument assembly utilizable in performing that method.

Laparoscopy involves the piercing of the abdominal wall and the insertion of a tubular member through the perforation. Various instruments may be inserted through the tubular member to perform surgical operations inside the abdomen.

Generally, upon the disposition of the first tubular member so that it traverses the abdominal wall, the abdominal cavity is pressurized to distend the abdominal wall and provide a safety region between the wall and the body organs inside the cavity. Moreover, several perforations are made. One perforation receives a laparoscope which enables visual monitoring of organs and surgical activities inside the abdominal cavity. Other perforations serve for the insertion of different surgical tools.

Laparoscopic surgical operations include such operations as for stapling together torn hernial tissues. However, to remove an organ or a portion of an organ such as a gall bladder or a kidney, a conventional incision must be made in the abdominal wall.

Laparatomic surgery provides several advantages over conventional incision-based surgery. The laparotomic perforations, in being substantially smaller than the incisions made during conventional operations, are less traumatic to the patient and provide for an accelerated recovery and convalescence. Hospital stays are minimized. Concomitantly, laparoscopic surgery is less time consuming and less expensive than conventional surgery for correcting the same problems.

OBJECTS OF THE INVENTION

An object of the present invention is to provide a laparotomic method for removing internal body organs or portions of body organs from a patient.

Another object of the present invention is to provide a surgical instrument assembly utilizable in performing such a method.

Another, more particular, object of the present invention is to provide such an instrument assembly which is simple to manufacture and therefore inexpensive.

A further particular object of the present invention is to provide such an instrument assembly which is easy to use.

SUMMARY OF THE INVENTION

A surgical instrument assembly comprises, in accordance with the present invention, a tubular member insertable through an opening in an abdominal wall of a patient and a flexible membrane disposed in a collapsed configuration at least partially inside the tubular member. The instrument assembly further comprises an ejection member engageable with the membrane for pushing the membrane in a distal direction and out of the tubular member into an internal body cavity of the patient. Elongate elements are connected to the membrane through the tubular member for closing the membrane about a body organ part upon a juxtaposition of the organ part and the membrane and for pulling the membrane from the body cavity of the patient and in a proximal direction through the tubular member.

Pursuant to another feature of the present invention, the instrument assembly also comprises a spreading device contactable with the membrane upon disposition thereof in the body cavity, for opening the membrane from the collapsed configuration into an at least partially opened configuration. The spreading device preferably takes the form of a grasping forceps insertable through another tubular member traversing a perforation in the abdominal wall of the patient.

Pursuant to another feature of the present invention, the instrument assembly additionally comprises a cutting, severing, pulverizing or macerating component contactable with the organ part for dividing the organ part while the organ part is inside the membrane. The dividing component may exemplarily take the form of an elongate rod insertable through the tubular member, a crushing or cutting forceps, an ultrasound generator, or a laser device.

Pursuant to yet another feature of the present invention, the instrument assembly further comprises an aspirator for applying a suction force through the tubular member to a chamber formed by the membrane upon closure thereof about the organ part by the elongate elements Preferably, the elongate elements include a plurality of flexible tensile members each attached at a distal end to the membrane and projecting at an opposite end out through a proximal end of the tubular member. The ejection member preferably comprises an elongate rod insertable through the tubular member.

The membrane is advantageously impermeable to microorganisms and made of a biologically inert synthetic resin material.

A surgical method in accordance with the present invention comprises the steps of (a) piercing an abdominal wall of a patient to form an opening in the abdominal wall, (b) inserting a tubular member through the opening, (c) pushing a biologically inert flexible membrane through the tubular member and into a body cavity of the patient, (d) opening the injected membrane from a collapsed configuration into an at least partially opened configuration, (e) juxtaposing the membrane and an internal organ part of the patient, (f) closing the membrane about the body organ part upon juxtaposition of the membrane and the organ part, and (g) drawing the membrane, together with the enclosed organ part, from the body cavity of the patient and in a proximal direction through the tubular member.

Generally, in performing the surgical method, the organ is severed prior to the juxtaposition step. Upon opening of the membrane and severing of the organ or organ part from the patient, the severed organ part is moved within the patient's body cavity until it rests on the opened membrane.

In accordance with the present invention, it may be recommended or even necessary in some cases to divide the organ part while maintaining the organ part inside the membrane, which has been closed about the organ part. This division of the organ parts is performed prior to the drawing of the membrane and the organ part out of the abdominal cavity through the tubular member.

The dividing of the organ part may be accomplished by any of several techniques well known in the surgical arts. For example, a crushing or cutting forceps member may be utilized to sever the organ part. A laser device, an ultrasonic energy generator or other device may be employed, in addition or as an alternative. In any case, the cutting instrument or device is inserted in a distal direction through the tubular member so that a distal end of the cutting instrument or device protrudes into a chamber formed by the closed membrane.

Upon the breaking of the organ part down into smaller pieces, some or all of the pieces may be withdrawn through the tubular member prior to the drawing of the membrane out through that member. The removal of the severed pieces or particulate organ matter may be accomplished partially or completely by aspiration. An aspirator tube may, for instance, be inserted through the tubular member after removal of the cutting device (forceps, laser fiber, etc.) therefrom.

Ejection of the folded or collapsed membrane from the tubular member is preferably implemented by inserting a rod member into the tubular member and shifting the rod member in a distal direction through the tubular member to thereby push the membrane out into the abdominal cavity of the patient.

The opening of the membrane upon the injection thereof into the patient's abdominal cavity is preferably accomplished includes the step of by gripping the membrane with a grasping forceps and pulling at least a portion of the membrane.

As described above, the membrane is connected to a plurality of elongate tensile members extending back out in a proximal direction through the tubular member through an aperture in the tubular member at a proximal end thereof. The closing of the membrane about the organ part and the drawing of the membrane and the organ part back out of the abdominal cavity through the tubular member is achieved by pulling the tensile members in a proximal direction through the tubular member.

It is to be noted that a surgical instrument assembly for performing a surgical method in accordance with the present invention essentially comprises a flexible membrane disposable in a collapsed configuration at least partially inside a laparotomic tubular member, as well as elongate members, preferably tensile elements such as strings or filaments, connected to the membrane. The tensile elements perform the function of (i) drawing the membrane about an internal body organ part of a patient upon (a) an ejection of the membrane through the tubular member and into a body cavity of the patient, (b) an opening of the membrane while in the body cavity, (c) a juxtaposition of the membrane and the organ part, and (ii) pulling the membrane from the body cavity of the patient and in a proximal direction through the tubular member.

A surgical technique in accordance with the present invention for enabling the removal of internal body organ parts will greatly reduce the expense, time and effort inherent in conventional incision-based surgery. Concomitantly, the trauma for the patient will, on the average, be considerably reduced. Patient recovery time will decrease, thereby making more beds available for other patients.

A surgical technique in accordance with the present invention is easy to implement and will not require inordinately extensive instruction or experience to master.

A surgical instrument assembly utilizable in performing a method in accordance with the present invention is simple to manufacture and therefore inexpensive.

DETAILED DESCRIPTION

Figure 1:
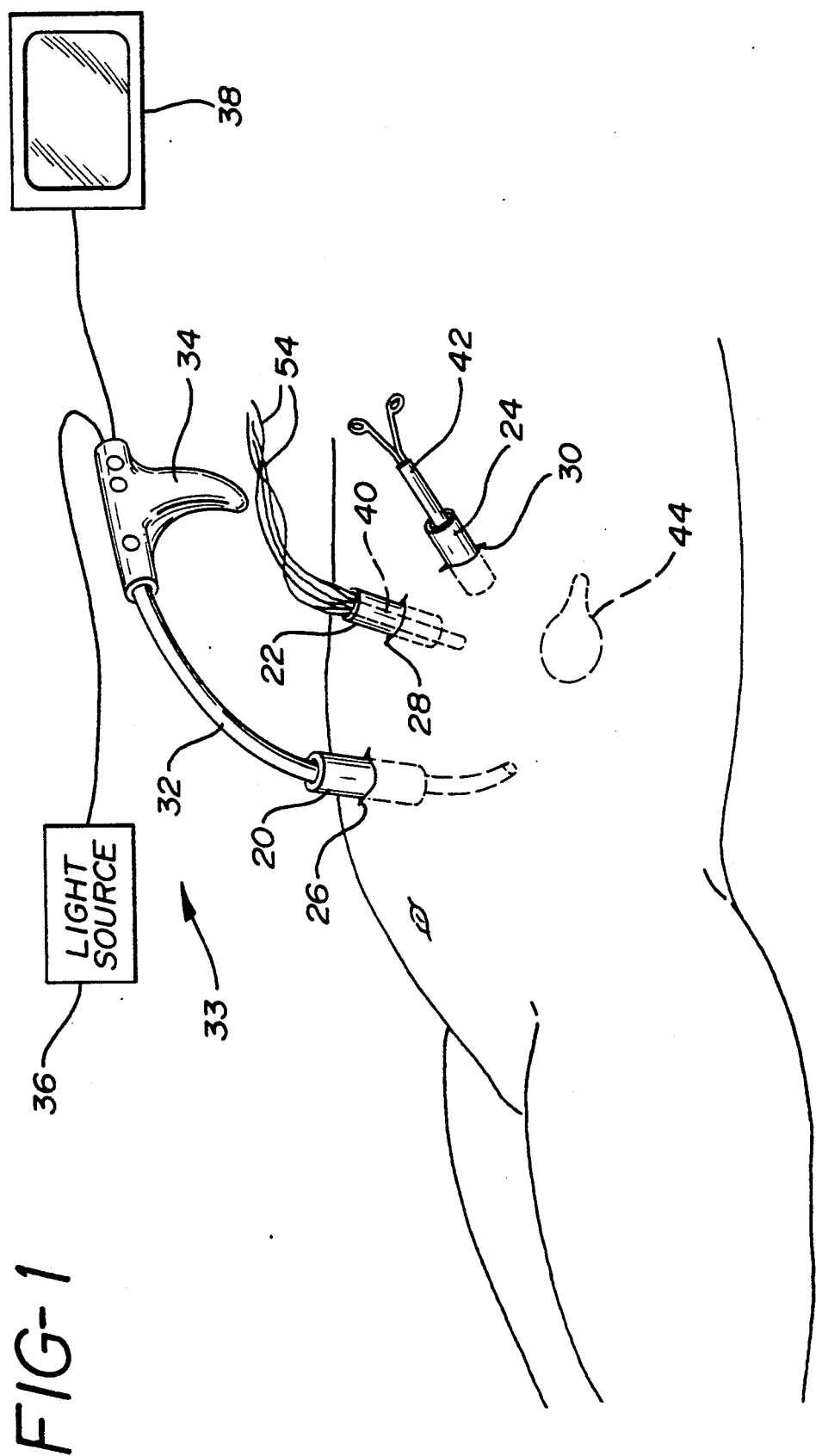
FIG. 1 is a schematic partial perspective view of a surgical instrument assembly in accordance with the present invention, in an exemplary operational configuration at the abdominal wall of a patient.

FIG. 1 shows a stage in a laparotomic surgical procedure wherein three tubular members 20, 22 and 24 have been inserted through respective puncture openings or perforations 26, 8 and 30 which have been formed at three spaced locations in the abdomen of a patient. One tubular member 20 serves as a laparoscopic tube and is longitudinally traversed by a flexible light guide portion 32 of a fiber optic type device 33. The fiber optic device further includes a handle or actuator member 34, a light source 36 and a television monitor 38. Light guide portion 32 carries visible electromagnetic radiation from light source 36 into the abdominal cavity of the patient and further carries reflected light or processed electronic signals back to monitor 38. Inasmuch as the details and operation of fiber optic device 33 is not are not considered to be part of the invention, that device is not further described hereinafter.

As shown in FIG. 1, tubular member 22 partially surrounds a collapsed or folded membrane or web 40 made of a biologically inert flexible synthetic resin material such as polyethylene or nylon which is impermeable to micro-organisms. Membrane or web 40 forms an essential feature of the invention and is described in greater detail hereinafter.

Tubular member 24 is an additional laparatomic element serving to enable the introduction into the patient's abdomen of instruments such as a grasping forceps 42.

A surgical operating technique will now be described with reference to FIGS. 2A through 2H. At the commencement of an operation for removing an internal body organ such as a gall bladder 44 (FIGS. 1, 2D, 2E), a sharp instrument such as a trocar 46 is used to pierce the abdominal wall 48 of a patient P. Upon the formation of perforation 28 (FIG. 1), tubular member 22 is inserted therethrough. A pressure source (not illustrated) is then connected to tubular member 22 and activated to pressurize the patient's abdominal cavity 50 (FIG. 2 et seq.).

Trocar 46 is also used to form perforations 26 and 30 (FIG. 1) through which tubular members 20 and 24 are inserted partially into abdominal cavity 50. Light guide portion 32 of fiber optic device 33 is then inserted through tubular member 20 and used to survey the internal landscape of the patient P.

Upon noting the arrangement of the internal body organs (not shown) of patient P, the operating surgeon inserts collapsed flexible membrane 40 into tubular member 22 and pushes the membrane through the tubular member with the aid of a pusher rod 52, as illustrated in FIG. 2. Pursuant to one specific technique in accordance with the present invention, collapsed membrane 40 is folded about a distal end of rod 52 and is inserted together with the rod's distal end into tubular member 22.

Attached to membrane 40 at spaced points along the periphery thereof are a plurality of flexible tensile elements 54 such as strings or filaments. The operating surgeon takes care to ensure that the free ends of filaments 54 remain extending outside of tubular member 22 at the proximal end thereof.

Figure 2A:
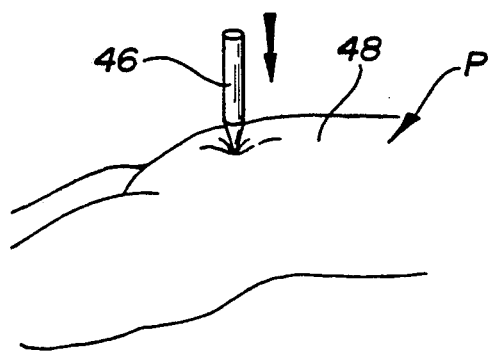
FIGS. 2A through 2E, 2G and 2H are schematic partial perspective views, partially in cross-section, showing successive stages in the use of an instrument assembly in accordance with the present invention.
Figure 2B:
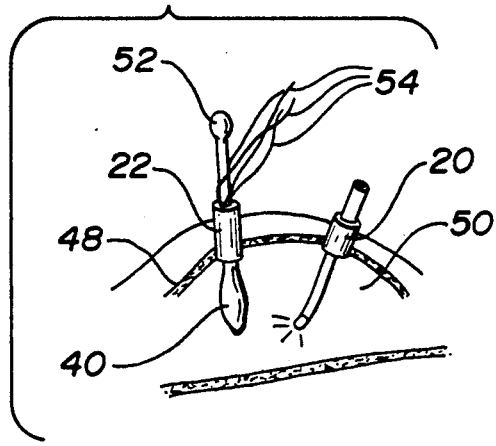
Figure 2C:
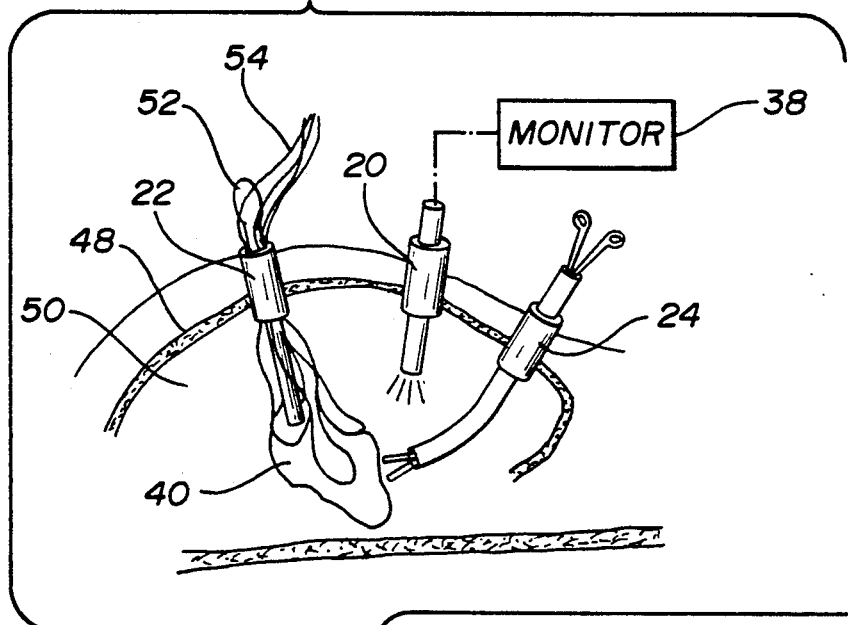
Figure 2D:
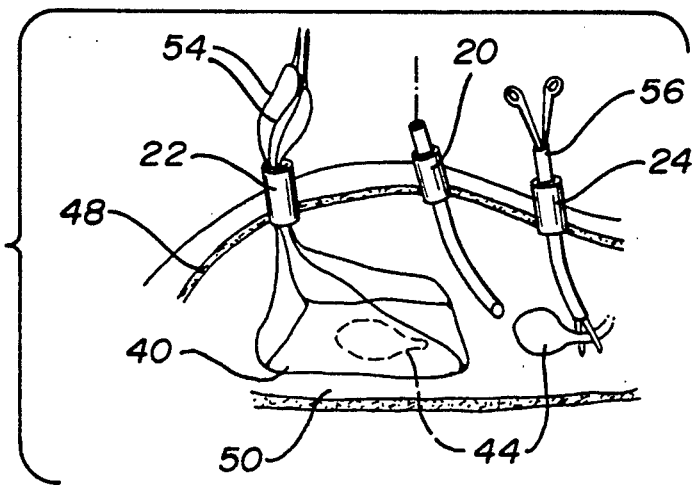

Upon the ejection of membrane 40 from tubular member 22 and the concomitant injection or disposition of the membrane inside abdominal cavity 50 (see FIG. 2C), grasping forceps 42 is inserted through tubular member 24 and actuated so as to grip a portion of membrane 40 and stretch the membrane until it assumes a substantially opened configuration shown in FIG. 2D.

At that juncture, the operating surgeon replaces grasping forceps 42, if necessary, by a cutting forceps 56 (FIG. 2D) and manipulates light guide portion 32 of fiber optic device 33 to view on monitor 38 the location and orientation of gall bladder 44. Forceps 56 are then used to sever bladder 44 from patient P. Observing the relative locations of membrane 40 and bladder 44 through the aid of fiber optic device 33, the surgeon manipulates grasping forceps 42 through tubular member 24 to move the severed bladder 44 into position in juxtaposition with membrane 40, as shown in phantom lines in FIG. 2D.

Upon the proper juxtaposition of bladder 44 and membrane 40, the surgeon draws filaments 54 in the proximal direction through tubular member 22, thereby closing membrane 40 about bladder 44. If bladder 44 is sufficiently deformable, the surgeon continues to exert a pulling force on filaments 54 to thereby draw both membrane 40 and bladder 44 tubular member 22 (see FIG. 2H). If, however, bladder is not deformable, for example owing to the presence of a number of gall stones, a crushing forceps 58 may be inserted through tubular member 22 and partially into a chamber formed by the closed membrane 40, as depicted in FIG. 2E.

Crushing forceps 58 is then manipulated to pulverize or divide the gall stones and other portions of bladder 44, if necessary. Upon reduction of the organ part to sufficiently small pieces by crushing forceps 58, the surgeon draws membrane 40 and its contents through tubular member 22.

Figure 2E:
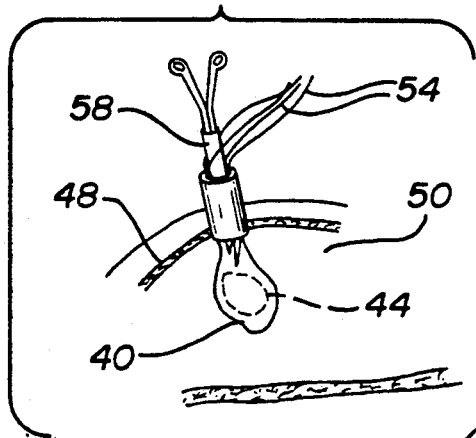
Figure 2F:
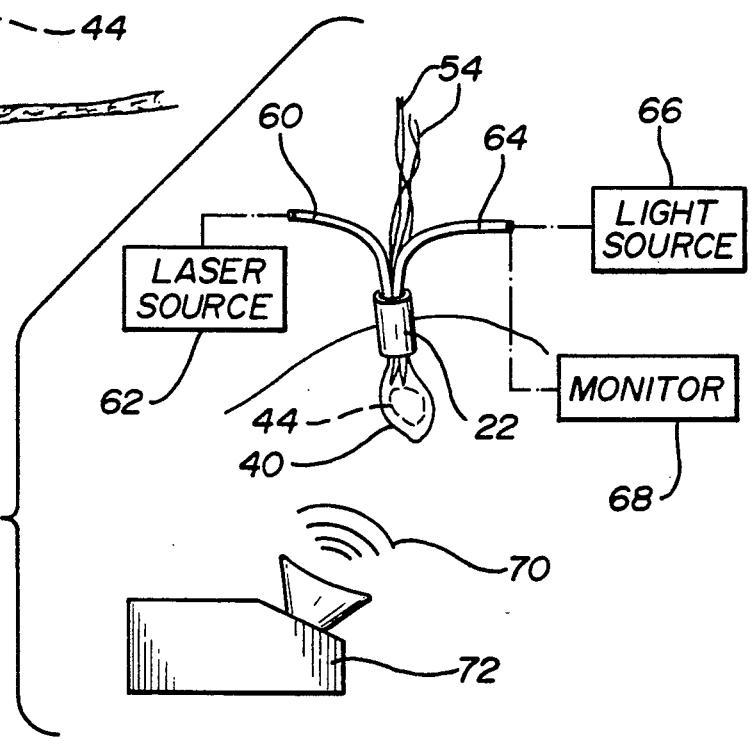
FIG. 2F is a schematic partial perspective view, partially in cross-section, showing an alternative instrument assembly to the instrument assembly shown in FIG. 2E.

As an alternative to the use of crushing forceps device 58 illustrated in FIG. 2E, FIG. 2F shows a fiber optic guide 60 inserted through tubular member 22 and connected at a proximal end to a laser source 62. A laser beam from source 62 is conducted by guide 60 through tubular member 22 to bladder 44. As further shown in FIG. 2F, another fiber optic guide 64 may also be inserted through tubular member 22 for enabling the operating surgeon to view the cutting operation inside membrane 40. Fiber optic guide 64 is connected at a proximal end to a light source 66 and a monitoring device 68. Monitoring device 68 may take the form of an eyepiece or a video monitor. Further electronic circuitry (not illustrated) is included in the case of video monitoring for changing optical intensities into an electrical signal controlling the energization of pixels on monitoring device 68.

The dividing of bladder 44 inside closed membrane 40 may be accomplished, alternatively or additionally, by focusing ultrasonic wave energy 70 from an ultrasonic generator 72 on the bladder inside the patient's body, as shown in FIG. 2F. It is to be noted, however, that the dividing of bladder 44 may be accomplished by virtually any technique and with any cutting, severing, pulverizing or macerating device.

Upon the dividing of bladder 44 into pieces, an aspiration tube or catheter 74 may be inserted through tubular member 22 to suck the bladder pieces out of membrane 40. As detailed schematically in FIG. 2G, aspiration catheter 74 is connected to a vacuum or suction source 76.

Other techniques are utilizable with the present invention. For example, prior to the aspirating of the pieces of bladder, a liquid may be deposited into membrane 40 for forming a slurry of the fractionated organ. The slurry may then be suction out via aspiration catheter 74.

Figure 2G:
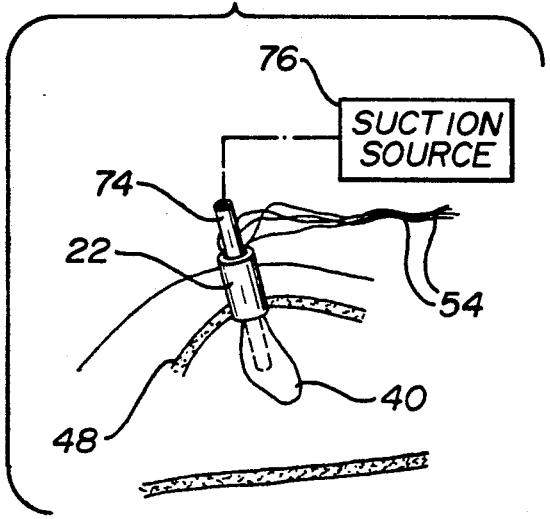
Figure 2H:
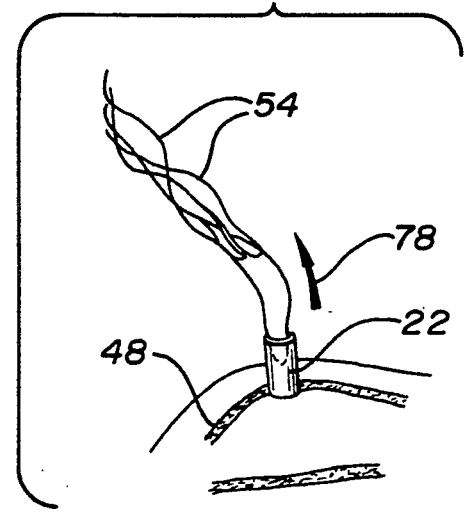

After the suctioning off of the severed bladder pieces as shown in FIG. 2G, membrane 40 is pulled from abdominal cavity 50 and through tubular member 22 via the application of tensile forces to filaments 54, as indicated in FIG. 2H by an arrow 78.

Figure 3:
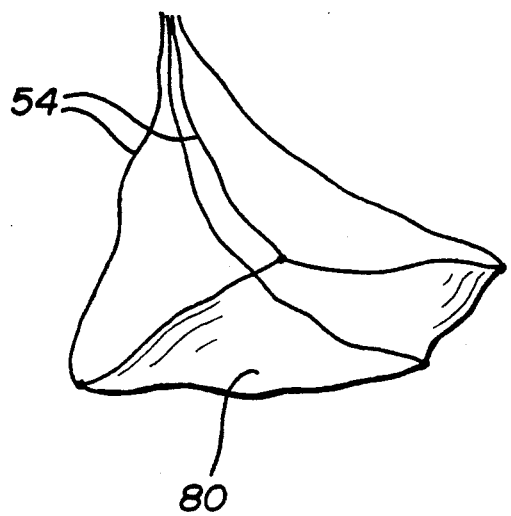
FIG. 3 is a perspective view of a membrane or web utilizable in performing a surgical method in accordance with the present invention, showing the membrane or web in an opened configuration.
Figure 4:
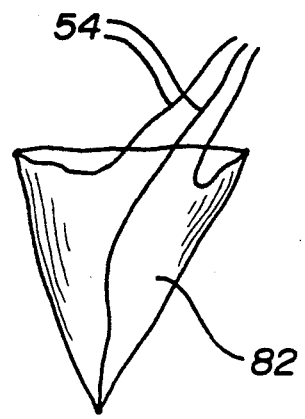
FIG. 4 is a top perspective view of another membrane or web utilizable in performing a surgical method in accordance with the present invention, showing the membrane or web in an opened configuration.
Figure 5:
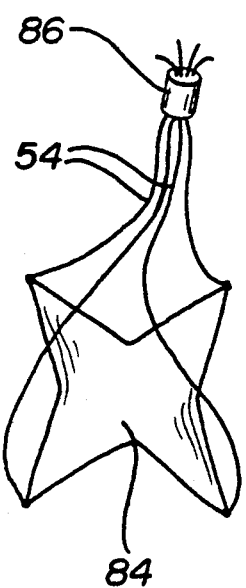
FIG. 5 is a top perspective view of yet another membrane or web utilizable in performing a surgical method in accordance with the present invention, showing the membrane or web in an opened configuration.

FIGS. 3, 4 and 5 depict a rectangular membrane 80, a triangular membrane 82, and a star-shaped membrane 84, respectively, all utilizable in performing a surgical operation in accordance with the present invention. Preferably, filaments 54 are attached to the corners of membranes 80, 82, and 84. As further illustrated in FIG. 5, filaments 54 may be connected to one another at their proximal ends by means of a clamp 86 or other coupling device. The clamp facilitates a grasping of all filaments 54 simultaneously, as well as an equal application of force to the various filaments.

Figure 6:
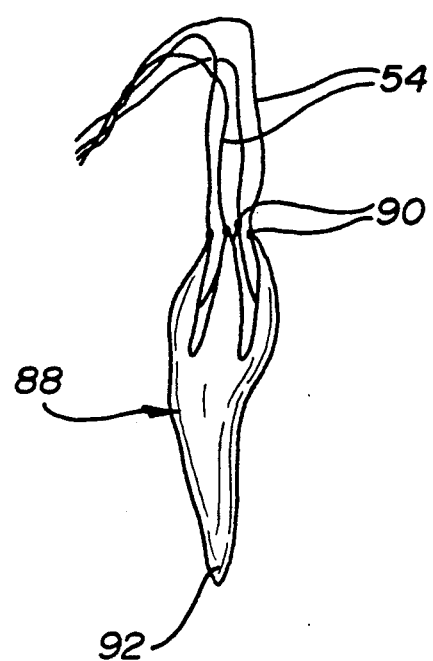
FIG. 6 is a side elevational view of yet another membrane or web in accordance with the present invention, showing the web in a collapsed or folded configuration.

As shown in FIG. 6, a flexible, microbe-impermeable, membrane 88 is folded into a collapsed configuration prior to insertion into tubular member 22. In the collapsed configuration, the corners 90 of membrane 88 are juxtaposed to one another while a central region 92 of the membrane is pulled in the opposite direction.

Figure 7:
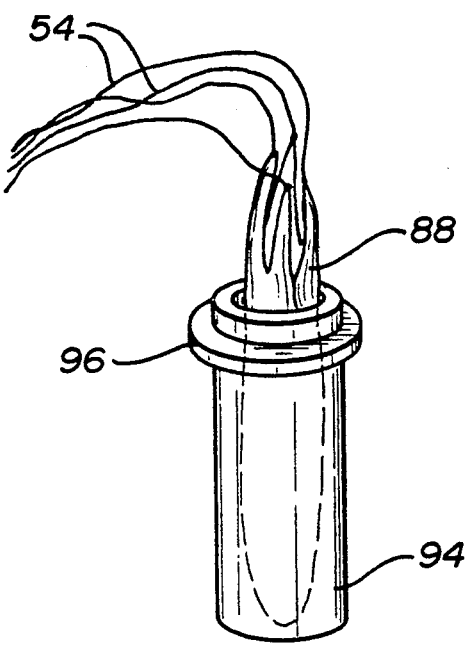
FIG. 7 is a perspective view of the collapsed membrane of FIG. 6 disposed inside a tubular member in accordance with the present invention.
Figure 8:
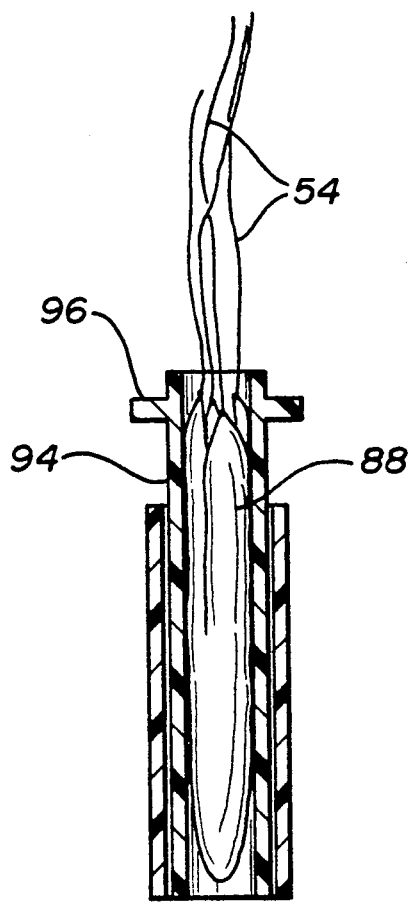
FIG. 8 is a longitudinal cross-sectional view of the membrane and tubular member of FIG. 7, showing them inserted inside a tubular laparotomic member.
Figure 9:
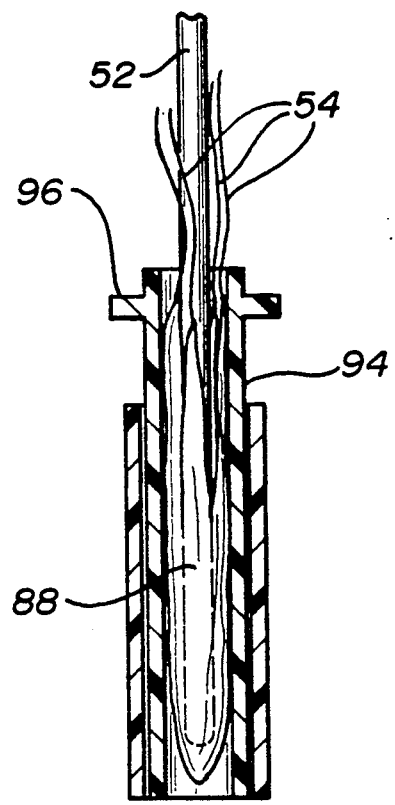
FIG. 9 is a longitudinal cross-sectional view of the membrane and tubular member of FIG. 7, showing a rod member inserted inside the membrane which in turn is inserted inside the tubular member, that entire assembly being inserted inside another tubular member, as in FIG. 8.

FIG. 7 shows an embodiment of the invention wherein the collapsed membrane 88 is preinserted into an additional tubular member 94. The additional tubular member 94 has an outside diameter smaller than the inside diameter of tubular member 22, whereby during a surgical operation in accordance with the present invention the additional tubular member may be inserted, together with membrane 88, inside tubular member 22, as shown in FIG. 8. As further illustrated in that drawing figure, additional tubular member 94 preferably has a length greater than the length of the collapsed membrane 88, whereby membrane remains completely inside tubular member 94 until ejection by rod member 52 (see FIGS. 2B and 9). Accordingly, tubular member 94 and the associated membrane 88 may be prepackaged and sold as a separated sterile unit. Alternatively, as shown in FIG. 9, membrane 88 and tubular member 94 may be sold as a unit together with rod member 52. Tubular member 94 is advantageously provided at a proximal end (FIGS. 7, 8 and 9) with an annular flange 96 or other finger hold for facilitating a holding of tubular member 94 during an ejection of membrane 88 via rod member 52.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are preferred by way of example to facilitate comprehension of the invention and should not be construed to limit the scope thereof.

What is claimed is:

1. A surgical kit comprising:
   a tubular member insertable through an opening in an abdominal wall of a patient;
   a flexible membrane disposed in a collapsed configuration at least partially inside said tubular member;
   ejection means engageable with said membrane for pushing said membrane in a distal direction and out of said tubular member into an internal body cavity of the patient;
   elongate means connected to said membrane through said tubular member for closing said membrane about a body organ part upon a juxtaposition of the organ part and said membrane and for pulling said membrane from the body cavity of the patient and in a proximal direction through said tubular member; and
   dividing means contactable with the organ part for dividing the organ part while the organ part is inside said membrane, said dividing means comprising a forceps member insertable through said tubular member.

2. A surgical method for removing an internal organ part from a patient, comprising the steps of:
   piercing an abdominal wall of a patient to form an opening in said abdominal wall;
   inserting a tubular member through said opening;
   pushing a biologically inert flexible membrane through said tubular member and into a body cavity of the patient;
   upon disposition of said membrane in said body cavity, opening said membrane from a collapsed configuration into an at least partially opened configuration;
   juxtaposing said membrane and the internal organ part of the patient;
   closing said membrane about said organ part upon juxtaposition of said membrane and said organ part; upon closure of said membrane about said organ part, drawing said membrane, together with at least a portion of the organ part, from the body cavity of the patient and in a proximal direction through said tubular member.

3. The method defined in claim 2, further comprising the step of severing said organ part from the patient prior to said step of closing.

4. The method defined in claim 3 wherein said step of severing is performed prior to said step of juxtaposing.

5. The method defined in claim 4 wherein said step of juxtaposing comprises the step of moving the severed organ pat towards said membrane.

6. The method defined in claim 3, further comprising the step of dividing said organ part while maintaining said organ part inside said membrane, said step of dividing being performed upon closure of said membrane about said organ part and prior to said step drawing.

7. The method defined in claim 6 wherein said step of dividing comprising the step of breaking said organ part up by use of a forceps member inserted through said tubular member.

8. The method defined in claim 6 wherein said step of dividing comprising the step of cutting said organ part into pieces by means of a laser device inserted through said tubular member.

9. The method defined in claim 6 wherein said step of dividing comprising the step of fractionalizing said organ part through the application of ultrasonic wave energy.

10. The method defined in claim 6, further comprising the step of withdrawing pieces of the divider organ part through said tubular member prior to said step of drawing.

11. The method defined in claim 10 wherein said step of withdrawing comprises the step of aspirating pieces of the divided organ part.

12. The method defined in claim 2 wherein said step of pushing is implemented by inserting a rod member into said tubular member and shifting said rod member in a distal direction through said tubular member, said membrane being disposed in a collapsed configuration at least partially inside said tubular member prior to said step of inserting.

13. The method defined in claim 2 wherein said step of opening includes the step of grasping said membrane with a grasping forceps and pulling at least a portion of said membrane.

14. The method defined in claim 2 wherein said membrane is connected to a plurality of elongate tensile members extending back out in a proximal direction through said tubular member through an aperture in said tubular member at a proximal end thereof, said step of closing comprising the step of pulling said tensile members in a proximal direction through said tubular member.

15. The method defined in claim 2 wherein said membrane is connected to a plurality of elongate tensile members extending back out in a proximal direction through said tubular member through an aperture in said tubular member at a proximal end thereof, said step of drawing comprising the step of pulling said tensile members in a proximal direction through said tubular member.

16. A surgical kit comprising:
   a tubular member insertable through an opening in an abdominal wall of a patient;

a flexible membrane disposed in a collapsed configuration at least partially inside said tubular member;

ejection means engageable with said membrane for pushing said membrane in a distal direction and out of said tubular member into an internal body cavity of the patient;

elongate means connected to said membrane through said tubular member for closing said membrane about a body organ part upon a juxtaposition of the organ part and said membrane and for pulling said membrane from the body cavity of the patient and in a proximal direction through said tubular member; and dividing means contactable with the organ part for dividing the organ part while the organ part is inside said membrane, said dividing means comprising an elongate rod insertable through said tubular member so that a distal end of said elongate rod is insertable inside said membrane upon a closure of said member and is engageable with the organ part to divide the organ part via said elongate means.

17. A surgical kit comprising: a tubular member insertable through an opening in an abdominal wall of a patient;

a flexible membrane disposed in a collapsed configuration at least partially inside said tubular member;

ejection means engageable with said membrane for pushing said membrane in a distal direction and out of said tubular member into an internal body cavity of the patient;

elongate means connected to said membrane through said tubular member for closing said membrane about a body organ part upon a juxtaposition of the organ part and said membrane and for pulling said membrane from the body cavity of the patient and in a proximal direction through said tubular member; and dividing means contactable with the organ part for dividing the organ part while the organ part is inside said membrane, said dividing means comprising a laser device insertable through said tubular member so that a distal end of said laser device in insertable inside said membrane upon a closure of said membrane via said elongate means.

18. A surgical kit comprising:

a tubular member insertable through an opening in an abdominal wall of a patient;

a substantially planar flexible membrane disposed in a collapsed configuration at least partially inside said tubular member, said member being convertible from said collapsed configuration to an expanded, substantially flattened configuration;

ejection means engageable with said membrane for pushing said membrane in a distal direction and out of said tubular member into an internal body cavity of the patient; and elongate means connected t said membrane through said tubular member for closing said membrane about a body organ pat upon a juxtaposition of the organ part and said membrane and for pulling said membrane from the body cavity of the patient and in a proximal direction through said tubular member.

19. The kit defined in claim 18, further comprising spreading means, contactable with said membrane upon disposition thereof in said body cavity, for opening said membrane from said collapsed configuration into an at least partially opened configuration.

20. The kit defined in claim 19 wherein said spreading means includes a grasping forceps.

21. The kit defined in claim 20, further comprising an additional tubular member insertable through an opening in an abdominal wall of a patient, said forceps being insertable at least partially into the body cavity of the patient through said additional tubular member.

22. The kit defined in claim 18 wherein said elongate means includes a plurality of elongate flexible tensile members each attached at a distal end to said membrane and extending through said tubular member.

23. The kit defined in claim 18 wherein said ejection means comprises an elongate rod insertable through said tubular member.

24. The kit defined in claim 18 wherein said membrane is impermeable to micro-organisms.

25. The kit defined in claim 18 wherein said membrane is made of a biologically inert synthetic resin material.

26. The kit defined in claim 18, further comprising aspirator means for applying a suction force through said tubular member to a chamber formed by said membrane upon closure thereof about said organ part by said elongate means.

27. The kit defined in claim 8, further comprising dividing means contactable with the organ part for dividing the organ part while the organ part is inside said membrane.

28. A surgical kit comprising:

a tubular member;

a biologically inert substantially planar flexible membrane disposed in a collapsed configuration at least partially inside said tubular member, said membrane being convertible from said collapsed configuration to an expanded, substantially flattened configuration; and elongate means connected to said membrane and extending from said membrane in a proximal direction and protruding from a proximal end of said tubular member.

* * * * *

UNITED STATES PATENT AND TRADEMARK OFFICE
CERTIFICATE OF CORRECTION

PATENT NO. : 5,074,867

DATED : December 24, 1991

INVENTOR(S) : Peter J. Wilk

It is certified that error appears in the above-identified patent and that said Letters Patent is hereby corrected as shown below:

In the Abstract, line 4, change "a" to --an--; line 18, change "provide" to --provided--.

Column 1, line 8, change "lapro-" to --laparo---; line 21, change "performation" to --perforation--; line 31, change "Laparatomic" to --Laparoscopic--.

Column 2, line 26, insert --.-- (period) after "elements".

Column 3, line 24, delete "includes the step of".

Column 4, line 48, change "8" to --28--; line 59, delete "is not".

Column 5, line 1, change "laparatomic" to --laparoscopic--.

Column 7, line 9, insert --the-- after "whereby"; line 28, change "preferred" to --proferred--.

Column 8, line 13, change "pat" to --part--.

Column 8, line 18, insert --of-- after "step".

UNITED STATES PATENT AND TRADEMARK OFFICE
CERTIFICATE OF CORRECTION

PATENT NO. : 5,074,867
DATED : December 24, 1991
INVENTOR(S) : Peter J. Wilk

It is certified that error appears in the above-identified patent and that said Letters Patent is hereby corrected as shown below:

Column 8, line 20 change "comprising" to --comprises--.

Column 8, line 24 change "comprising" to --comprises--.

Column 8, line 29 change "comprising" to --comprises--.

Column 8, line 33 change "divider" to --divided--.

Column 10, line 3 change "t said" to --to said--; line 5, change "pat" to --part--.

Column 10, line 39 change "8" to --18--.

Signed and Sealed this

Eighth Day of June, 1993

Attest:

MICHAEL K. KIRK

*Attesting Officer*   Acting Commissioner of Patents and Trademarks